(12) United States Patent
Sleeman et al.

(10) Patent No.: US 7,357,044 B2
(45) Date of Patent: Apr. 15, 2008

(54) SAMPLE COLLECTION DEVICE AND METHOD OF USING SAID DEVICE

(75) Inventors: Richard Sleeman, Bristol (GB); John George Luke, Bristol (GB); Samantha Ollerton, Cheltenham (GB)

(73) Assignee: Mass Spec Analytical Ltd., Bristol (GB)

( * ) Notice: Subject to any disclaimer, the term of this patent is extended or adjusted under 35 U.S.C. 154(b) by 238 days.

(21) Appl. No.: 11/126,824

(22) Filed: May 11, 2005

(65) Prior Publication Data

US 2005/0274205 A1 Dec. 15, 2005

(30) Foreign Application Priority Data

May 11, 2004 (GB) ................... 0410493.1

(51) Int. Cl.
*G01N 1/00* (2006.01)

(52) U.S. Cl. ................... 73/864.71; 73/863.12

(58) Field of Classification Search ............. 73/864.71
See application file for complete search history.

(56) References Cited

U.S. PATENT DOCUMENTS

| 3,593,583 | A | * | 7/1971 | Anderson et al. ........ 73/863.11 |
| 4,063,895 | A | * | 12/1977 | Neti et al. ...................... 436/2 |
| 4,242,107 | A | * | 12/1980 | Jenkins ............................. 95/8 |
| 4,584,887 | A | * | 4/1986 | Galen ....................... 73/863.31 |
| 4,982,616 | A | * | 1/1991 | Koch et al. ............... 73/864.81 |
| 5,083,019 | A | | 1/1992 | Spangler |
| 5,109,691 | A | | 5/1992 | Corrigan et al. |
| 5,123,274 | A | * | 6/1992 | Carroll et al. ........... 73/863.12 |
| 5,162,652 | A | | 11/1992 | Cohen et al. |
| 5,212,991 | A | * | 5/1993 | Suzanne et al. ......... 73/863.11 |
| 6,192,766 | B1 | * | 2/2001 | G.ang.rdhagen et al. . 73/863.12 |
| 6,397,658 | B1 | * | 6/2002 | Villettaz et al. ........... 73/19.12 |
| 2002/0148305 | A1 | * | 10/2002 | Danylewych-May et al. ....................... 73/863.21 |
| 2004/0053421 | A1 | | 3/2004 | Nguyen et al. |

FOREIGN PATENT DOCUMENTS

GB 2393403 3/2004

* cited by examiner

*Primary Examiner*—Robert Raevis
(74) *Attorney, Agent, or Firm*—Gardere Wynne Sewell LLP

(57) ABSTRACT

A sample collection device for use with a chemical analyzer, the device comprising a sample collecting assembly having at least one sampling medium and a sample desorbing assembly arranged to receive the sampling medium therein, the sample collecting assembly and sample desorbing assembly being movable with respect to one another between a sample collecting configuration in which the sampling medium is substantially exposed and a sample desorbing configuration in which the sampling medium is substantially housed within the sample desorbing assembly.

19 Claims, 4 Drawing Sheets

SAMPLE COLLECTION DEVICE AND METHOD OF USING SAID DEVICE

CROSS-REFERENCE TO RELATED APPLICATION

This application claims the benefit of Patent Application No. GB 0410493.1 filed May 11, 2004.

BACKGROUND OF THE INVENTION

The present invention relates to the collection of samples, including uses and observations made thereof.

The ability to accurately and reliably determine the presence or otherwise of a particular sample (e.g., compound, agent, molecule, chemical, gas, toxin, metal, drug) on an everyday object is of significant importance to customs and police forces around the world. The samples of interest include illicit drugs and explosives and it is their detection in both a forensic context and with regard to the detection of contraband or tariff evasion that is of interest to police and custom forces respectively. Generally, the samples of interest are likely to be present only in extremely small, or trace amounts. Consequently, extremely sensitive chemical analysis techniques are employed to determine the presence or otherwise of a particular compound (target compound analysis).

One such analytical approach known from the prior art is to use a Tandem Mass Spectrometer to chemically analyse a collected sample. However, the prior art techniques for analysing collected samples, and more particularly in the preparation of the samples prior to analysis by the Mass Spectrometer, can be both complex and time consuming. For example, bank notes are sampled by taking bundles of bank notes and shaking them over a sheet of aluminium foil. Any particles deposited on the foil are then vacuumed up, the vacuum including a removable filter, and the filter sampled using the Tandem Mass Spectrometer. To sample each filter generally requires extensive sample preparation and sometimes chemical treatment prior to analysis. Consequently, the sample collection process is both complex and time consuming.

Whilst such sample collection techniques may be appropriate when a suspect object has already been identified, for example by virtue of being found in the possession of a suspected criminal, they are not applicable for collecting samples from a large number of items to identify a suspect item. A typical example of where such a requirement is experienced is in checking the baggage of travellers in an airport, train station, a cruise ship embarkation terminal or any other transportation terminal or security check point in which large numbers of people and their bags need to be processed quickly and efficiently. In such circumstances the prior art sampling techniques and apparatus do not allow individual items of baggage to be sampled in a time effective manner.

One of the difficulties in sampling certain objects (e.g., baggage) for the presence of unwanted samples (e.g., explosives, drugs, toxins, illicit compounds, counterfeit materials, gases, etc.) is actually retrieving a sample from the object and presenting those samples to a suitable detector, such as a Mass Spectrometer or other device. In many cases, it is difficult to get into the various corners and recesses of the objects or items to be sampled, whilst avoiding cross contamination from one object or item to another. Similarly, it is difficult to remove the samples from the sampling devices and achieve acceptable levels of sensitivity to various particles of the sample. Accordingly, there remains a need for improved methods and devices for sampling objects.

SUMMARY OF THE INVENTION

The present invention solves many problems associated with current devices and methods of sampling.

Generally, and in one form of the present invention provides a sample collection device for use with a chemical analyzer, the device comprising a sample collecting assembly having at least one sampling medium and a sample desorbing assembly arranged to receive the sampling medium therein, the sample collecting assembly and sample desorbing assembly being movable with respect to one another between a sample collecting configuration in which the sampling medium is substantially exposed and a sample desorbing configuration in which the sampling medium is substantially housed within the sample desorbing assembly. The sampling medium may include a vapor adsorbent material and/or a frangible portion. The sampling medium may be attached to a sample medium carrier by means of a frangible fastener. The sample collecting assembly may be arranged to be rotatably driven. The sample desorbing assembly may also have a heating apparatus arranged to heat the sampling medium and/or an item to be sampled. The heating apparatus may include a hot air blower. The sample desorbing assembly may also have one or all of the following: a feed conduit arranged to be coupled to a chemical analyzer; an extendable member arranged to be driven between a first position and a second position, such that in the second position the extendable member encloses the sampling medium; and/or a closure member movable between an open and closed position, such that in the closed position the sample desorbing assembly defines a substantially closed cavity, the cavity being arranged to receive the sampling medium therein. The sample collecting assembly may also be arranged to be driven between first and second positions, such that in the second position the sampling medium is housed within the sample desorbing assembly The present invention also provides is provided a method of sample collection for chemical analysis, the method comprising providing a sample collecting assembly having at least one sampling medium, providing a sample desorbing assembly arranged to receive the sampling medium therein, bringing the sampling medium into contact with an item to be sampled and imparting relative motion between the item and the sampling medium, moving the sample collecting assembly and sample desorbing assembly with respect to one another such that the sampling medium is received within the sample desorbing assembly, desorbing the sample medium, and conveying desorbed vapour to a chemical analysis device. The sampling medium may be driven in rotation to impart the relative motion between the sampling medium and the item to be sampled and/or may be heated. Similarly, the item to be sampled may be heated. At least a portion of the sample desorbing assembly is driven between a first and second position, the sample desorbing assembly substantially enclosing the sampling medium in the second position.

The present invention further provides for a sample analysis system comprising a chemical analysis device coupled to one or more sample collection devices. The one or more sample collection devices may be further arranged to be operated in accordance with a predetermined sequence.

Those skilled in the art will further appreciate the above-noted features and advantages of the invention together with

BRIEF DESCRIPTION OF SEVERAL VIEWS OF THE DRAWINGS

For a more complete understanding of the features and advantages of the present invention, reference is now made to the detailed description of the invention along with the accompanying figures in which corresponding numerals in the different figures refer to corresponding parts.

DETAILED DESCRIPTION

Although making and using various embodiments of the present invention are discussed in detail below, it should be appreciated that the present invention provides many inventive concepts that may be embodied in a wide variety of contexts. The specific aspects and embodiments discussed herein are merely illustrative of ways to make and use the invention, and do not limit the scope of the invention.

Figure 1:
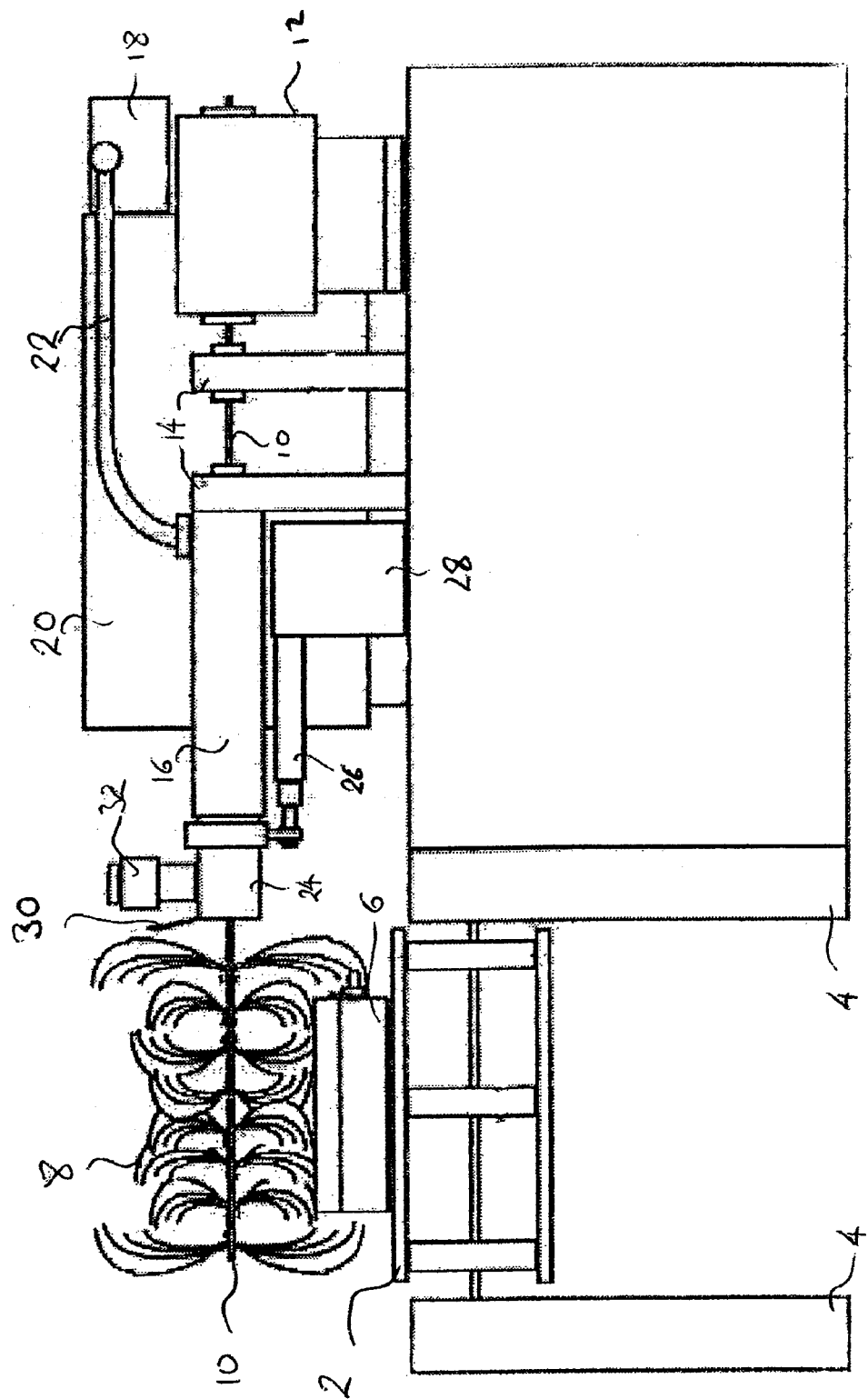
FIG. 1 illustrates a device in accordance with an embodiment of the present invention in a baggage sampling mode of operation.

FIG. 1 illustrates a sample collection and analysing system in accordance with an embodiment of the present invention. A conveyor belt 2 is mounted on a pair of supports for and is rotatably driven in a conventional manner. Items of baggage 6, such as suitcases, briefcases or the like, that have been placed on the conveyor belt 2 are moved along by the conveyor in a conventional manner. Mounted above the conveyor belt 2 is a set of flail adsorbers 8 fastened to a flail drive shaft 10. The flail drive shaft is arranged to be substantially perpendicular to the direction of travel of the conveyor belt 2. In preferred embodiments of the present invention a plurality of flail adsorbers are mounted on the flail drive shaft 10, with the adsorbers 8 being evenly spaced along both the length of the flail drive shaft and around its circumference. The flail adsorbers 8 preferably comprise strands or strips of a suitable adsorber material. In preferred embodiments the material is able to both swab for particles of material and also adsorb vapours into the flail material, although in other embodiments the flail material may provide only one of these functions. In alternative embodiments, the flail adsorbers 8 may comprise separate sets of flail material, with a first set being of material suitable for swabbing for particles of material and second flail material being suitable for adsorbing vapours. The flail material may contain molecular sieves designed to differentiate between different sample materials.

The flail drive shaft 10 is connected to a flail drive motor 12 such that the flail drive shaft 10 and the flail adsorbers 8 can be driven in rotation. If required, depending upon the length of the flail drive shaft 10 and arrangement of other components, one or more drive shaft bearing blocks 14 may be provided to support the flail drive shaft 10.

The flail drive shaft 10 passes through an elongate collector unit 16 that has an internal cavity formed therein. The internal cavity of the collection unit 16 is in communication with the input apparatus 18 of a Tandem Mass Spectrometer 20, via a feed conduit 22. The Tandem Mass Spectrometer 20 is of a kind known in the prior art, and as such includes a plenum chamber into which a desorbed sample is transferred from the input apparatus 18. An ioniser needle assembly comprising a high voltage electrode, e.g. at 8 kV, is mounted within the plenum chamber. The corona discharge of the high voltage electrode causes immediate ionisation of a proportion of any substances entering the main chamber for analysis in the known manner. It will of course be appreciated that other ionisation techniques may also be used.

In use, the flail drive shaft and flail adsorbers are preferably driven in rotation by the flail drive motor such that the individual flail adsorbers 8 are repeatedly swept over, and in contact with, the baggage item 6 as it is passed under the rotating flail adsorbers 8 on the conveyor 2. In alternative embodiments the flail adsorbers and flail drive shaft 10 may be mounted on an actuator arranged to vary the height of the flail drive shaft 10 and adsorbers 8 in relation to the conveyor 2. One or more sensors may be provided to detect the size of the baggage item 6 on the conveyor 2 and to adjust the height of the flail adsorbers and drive shaft 10 by means of the actuator so as to maintain an optimum distance between the flail adsorber 8 and the upper surface of the item baggage 6. In some embodiments, the flail adsorbers 8 are frangible, that is they can be torn off the flail drive shaft 10 in the event of the adsorber 8 being snagged on the baggage item 6. The flail adsorbers 8 may alternatively be formed with one or more perforated lines running across the width of the flail adsorbers and spaced apart at intervals along their length, such that if the flail adsorber 8 is snagged on the baggage item 6, the adsorber 8 is likely to tear along one of the perforated lines. A further envisaged arrangement is for the flail adsorbers 8 to be attached to the drive shaft 10 in such a manner that the attachment would fail if an excessive force was applied to it, as would be the case if the flail adsorber 8 was snagged on the baggage item 6.

Figure 2:
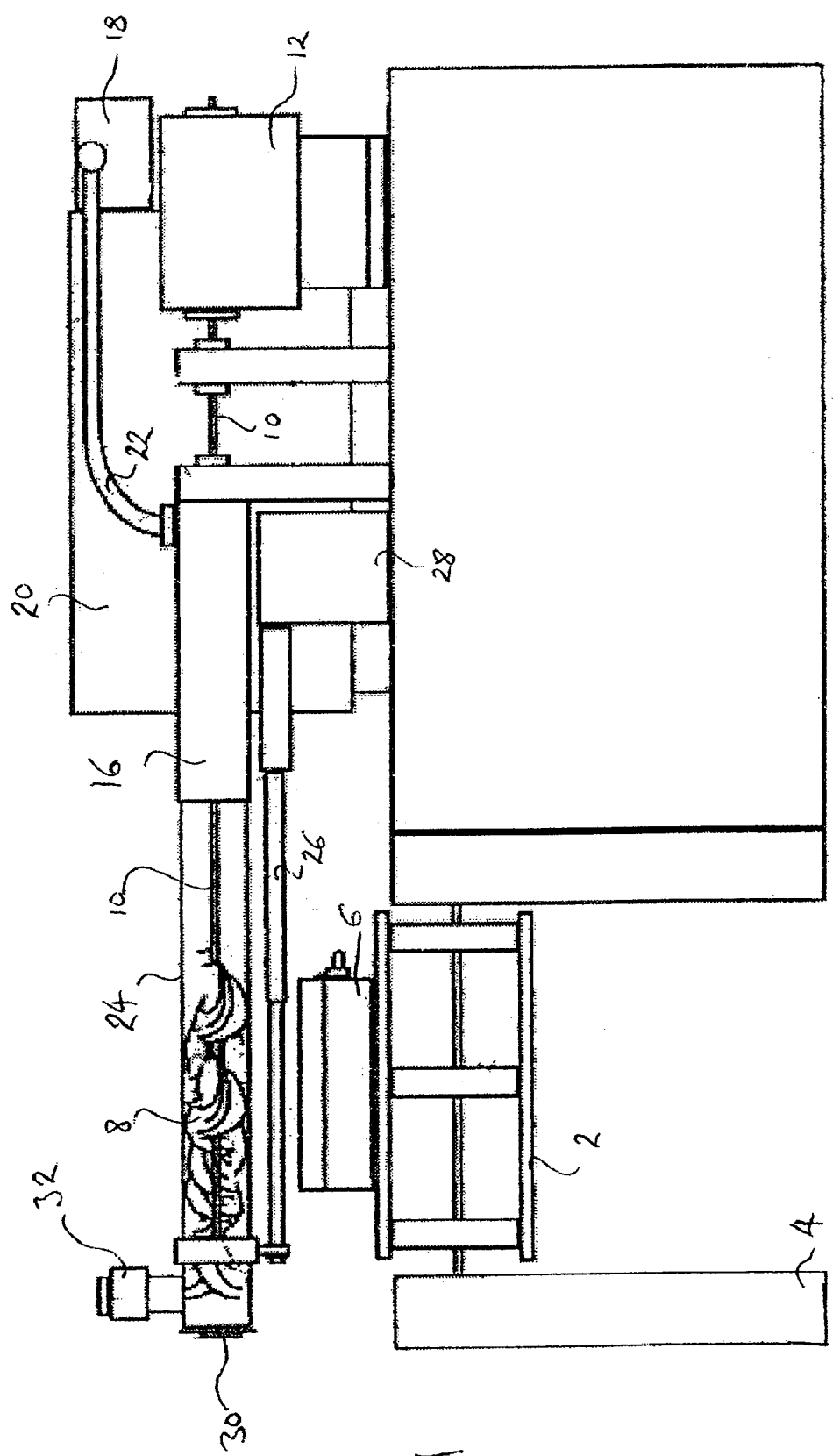
FIG. 2 illustrates the sampling and analysis device of FIG. 1 in a sample analyzing mode of operation.

On completion of the sample collection process, i.e. when the individual item baggage 6 has been conveyed past the revolving flail adsorbers 8, a telescopic extension 24 of the collector unit 16, shown in the retracted position in FIG. 1, is extended by means of a pneumatic or hydraulic piston 26 driven by a hydraulic or pneumatic driving unit 28. In alternative embodiments, the hydraulic or pneumatic piston 26 may be replaced with any other form of linear actuator, for example such as an electrically driven worm drive. As shown in FIG. 2, the flexible flail adsorbers 8 are thus enclosed by the collector extension tube 24, with the extension tube being preferably closed off by means of an end cap 30, which may be manually or automatically closed.

The sample particles and adsorbed material are then removed by desorption into the interior of the collector 16 and subsequently passed to the mass spectrometer for analysis by means of the feed conduit 22. To achieve satisfactory desorption the flail adsorbers 8 are preferably heated. Such heating may occur by heating the internal cavity of the collection unit 16, and the telescopic extension 24 by, for example, heating elements (not shown) placed within the extension tube and/or collection unit 16. However, in preferred embodiments the flail adsorbers 8 are heated whilst the extension tube 24 of the collector unit 16 is in the retracted position (shown in FIG. 2) by means of a hot air blower 32 such that the flail adsorbers 8 are heated to a temperature sufficient for desorption to occur within the extended extension tube 24 and the collector unit 16 without further heating. It is also preferred that the hot air blower 32 is arranged to heat the baggage item 6 as it passes under the rotating flail in addition to the flail adsorbers 8. Heating the baggage item 6 in this manner will tend to liberate any explosives or other compounds of interest, such that the liberated vapours can be easily adsorbed by the flail adsorbers 8. In this mode of operation the sampling apparatus is operating as both a vapour and particle detector.

Figure 3A:
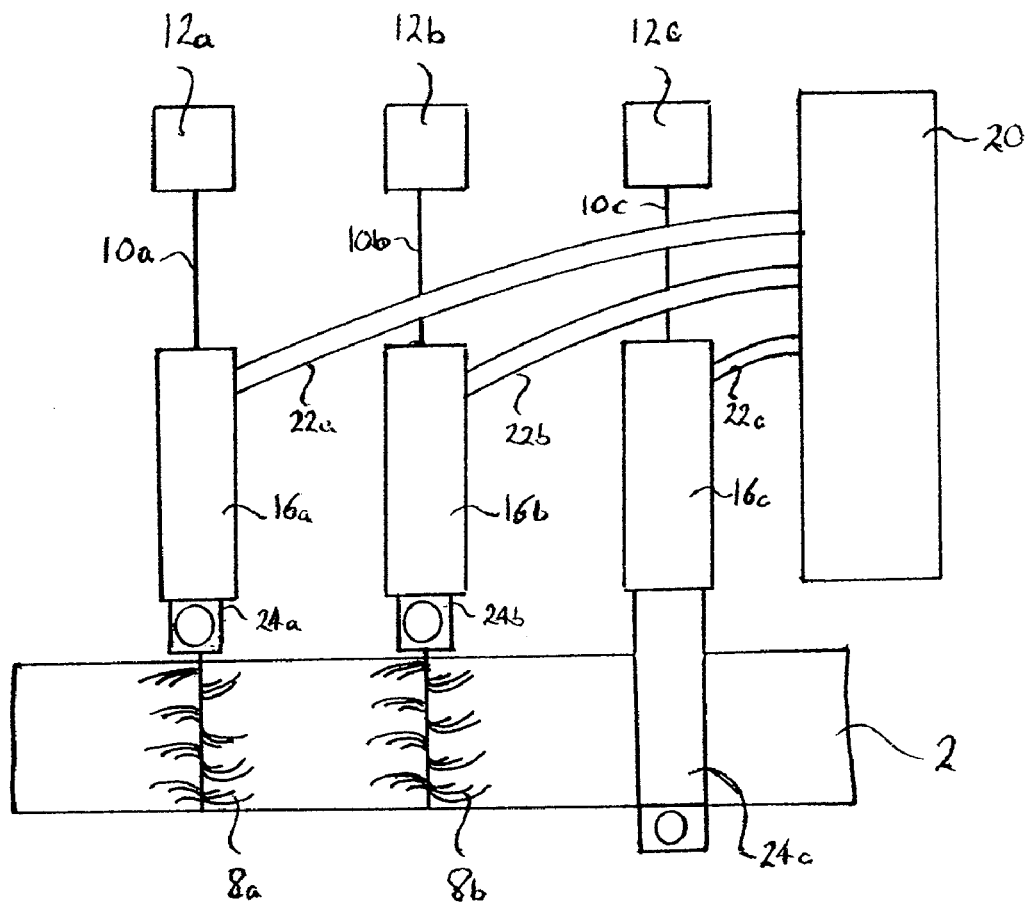
FIGS. 3A and 3B illustrate in plan views sampling and analysis devices in accordance with further embodiments of the present invention having multiple sample collection stations.
Figure 3B:
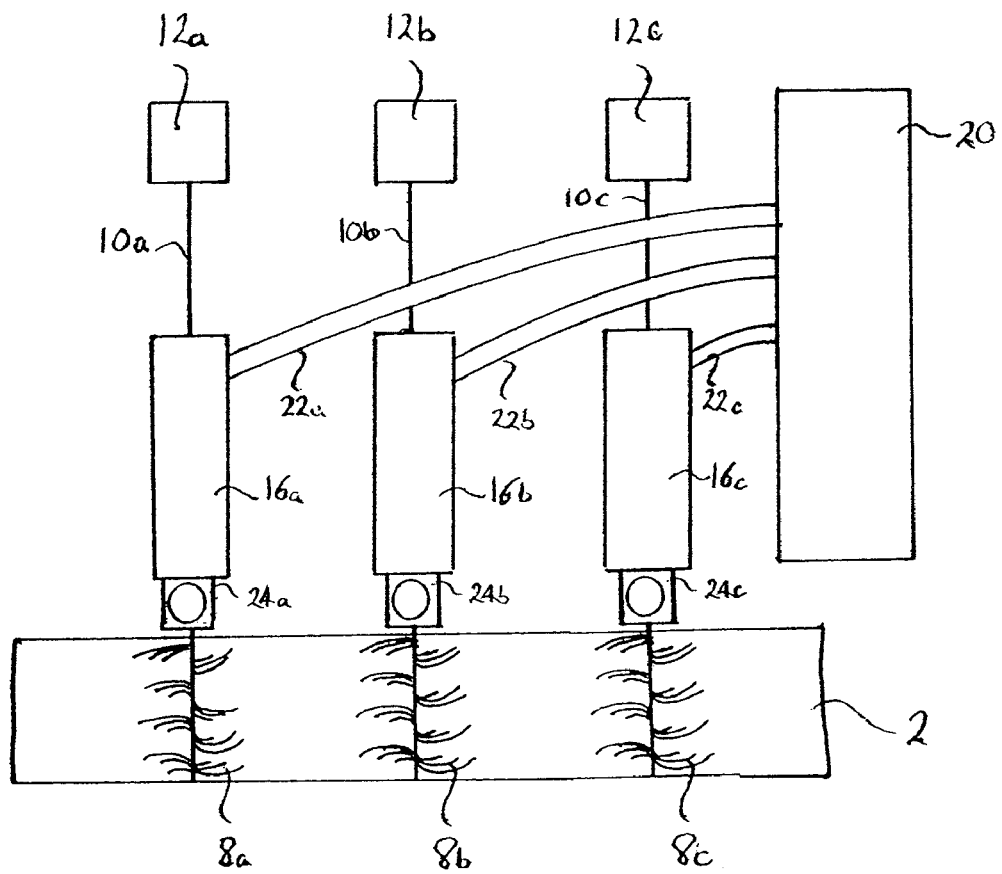

Further embodiments of the sampling and analysis system of the present invention are shown in plan view in FIGS. 3A and 3B. In this embodiment three separate revolving flail adsorber sets 8a, 8b, 8c are provided spaced apart along a length of the conveyor belt 2. Each flail adsorber 8 has a respective collector unit 16a, 16b, 16c and corresponding extension tube 24a, 24b, 24c in an identical manner to that described previously with reference to FIGS. 1 and 2. Similarly, the drive shaft 10a, 10b, 10c of each of the flail adsorbers is driven by a respective drive motor 12a, 12b, 12c, although in further embodiments a single drive motor may be provided to drive all three drive shafts via an appropriate arrangement of gears and/or drive belts. The collector unit of each flail adsorber is connected, via respective feed conduits 22a, 22b, 22c, to a single tandem mass spectrometer 20. Although separate feed conduits are shown in FIG. 3, alternative embodiments may include a manifold arrangement and appropriate valving such that only a single connection to the mass spectrometer 20 is required.

In use, the extension/retraction of the individual extension tubes 24a, 24b, 24c is sequenced under control of an appropriate control unit (not shown) such that one or more of the flail adsorbers is enclosed by a respective extension tube and undergoes desorption whilst one or more of the remaining flail adsorbers is operative to collect samples from baggage items passing underneath the flail adsorbers on the conveyor belt 2. In the arrangement shown in FIG. 3, the right hand most flail adsorber is being desorbed within the extended extension tube 24c, whilst the remaining two adsorbers 8a, 8b are represented as collecting samples from baggage items on the conveyor belt 2. However, it will be appreciated that the sequencing of the various flail adsorber units can be varied as desired, in accordance with parameters such as the speed of the conveyor belt 2, the number and spacing of baggage items on the conveyor belt and the time taken to desorb a flail adsorber set. The sequencing of the adsorbers may also depend upon the number of adsorbers provided, which may be greater than or less than the number shown in FIG. 3.

In further embodiments of the present invention the drive shaft 10 of the adsorber assembly may itself be telescopic and arranged to be retractable into the collector unit 16 to perform the desorption process. In such an embodiment the collector unit 16 would be of fixed length, i.e. there will be no requirement for the extension tube 24 and associated drive unit. In other embodiments, the rotating flail assembly 8 may be replaced by a non-rotating assembly from which one or more portions of adsorbent material hang such that baggage items 6 carried past the hanging adsorbent material by the motion of the conveyor belt 2 are brought into contact with the adsorbent material. The arm from which such adsorbent material hangs may be arranged to reciprocate back and forth in a direction substantially perpendicular to the motion of the conveyor belt so as to effectively wipe the adsorbent material over any baggage item 6 on the conveyor belt 2. Such an arrangement may be preferred for the sampling of items other than baggage items where the items to be sampled are of a fragile nature and could be damaged by the action of the previously described rotating flail apparatus.

Additional objects, advantages and novel features of the invention as set forth in the description, will be apparent to one skilled in the art after reading the foregoing detailed description or may be learned by practice of the invention. The objects and advantages of the invention may be realized and attained by means of the instruments and combinations particularly pointed out here.

What is claimed is:

1. A sample collection device for use with a chemical analyzer, the device comprising:
   a sample collecting assembly having at least one sampling medium; and
   a sample desorbing assembly arranged to receive the sampling medium therein, the sample collecting assembly and sample desorbing assembly being movable with respect to one another between a sample collecting configuration in which the sampling medium is substantially exposed and a sample desorbing configuration in which the sampling medium is substantially housed within the sample desorbing assembly, the sample collecting assembly including a mechanical drive mechanism arranged to mechanically drive the sampling medium into physical contact with an object from which a sample is to be collected and to mechanically drive the sampling medium in motion relative to the object.

2. The sample collection device of claim 1, wherein the sampling medium comprises a vapour adsorbent material.

3. The sample collection device of claim 1, wherein the sampling medium comprises a frangible portion.

4. The sample collection device of claim 1, wherein the sampling medium is attached to a sample medium carrier by means of a frangible fastener.

5. The sample collection device of claim 1, wherein the sample collecting assembly is arranged to be rotatably driven.

6. The sample collection device of claim 1, wherein the sample desorbing assembly further comprises a heating apparatus arranged to heat the sampling medium.

7. The sample collection device of claim 6, wherein the heating apparatus heats an item to be sampled.

8. The sample collection device of claim 6, wherein the heating apparatus includes a hot air blower.

9. The sample collection device of claim 1, wherein the sample desorbing assembly further comprises an extendable member arranged to be driven between a first position and a second position, such that in the second position the extendable member encloses the sampling medium.

10. The sample collection device of claim 1, wherein the sample collecting assembly is arranged to be driven between first and second positions, such that in the second position the sampling medium is housed within the sample desorbing assembly.

11. The sample collection device of claim 1, wherein the sample desorbing assembly further comprises a feed conduit arranged to be coupled to a chemical analyzer.

12. The sample collection device of claim 1, wherein the sample desorbing assembly further comprises a closure member movable between an open and closed position, such that in the closed position the sample desorbing assembly defines a substantially closed cavity, the cavity being arranged to receive the sampling medium therein.

13. A method of sample collection for chemical analysis, the method comprising:
   providing a sample collecting assembly having at least one sampling medium;
   providing a sample desorbing assembly arranged to receive the sampling medium therein;

mechanically driving the sampling medium into physical contact with an object from which a sample is to be collected and mechanically driving the sampling medium in motion relative to the object;

moving the sample collecting assembly and sample desorbing assembly with respect to one another such that the sampling medium is received within the sample desorbing assembly;

desorbing the sample medium; and conveying desorbed vapour to a chemical analysis device.

14. The method of claim 13, wherein the sampling medium is driven in rotation.

15. The method of claim 13, wherein the sampling medium is heated.

16. The method of claim 13, wherein the item to be sampled is heated.

17. The method of claim 13, wherein at least a portion of the sample desorbing assembly is driven between a first and second position, the sample desorbing assembly substantially enclosing the sampling medium in the second position.

18. A sample analysis system comprising a chemical analysis device coupled to one or more sample collection devices of claim 1.

19. The sample analysis system of claim 18, wherein the one or more sample collection devices are arranged to be operated in accordance with a predetermined sequence.

* * * * *